(12) United States Patent
Elgie et al.

(10) Patent No.: US 7,188,772 B2
(45) Date of Patent: Mar. 13, 2007

(54) METHOD FOR DETERMINING AN OPTIMAL ERGONOMIC SETUP

(75) Inventors: Richard James Elgie, Los Gatos, CA (US); Timothy James Brophy, Redwood City, CA (US); Adam Ackley Carr, Brookline, MA (US); David Pitcher, Worcester, MA (US); Vito Lore, Providence, RI (US)

(73) Assignee: ACCO Brands USA LLC, Lincolnshire, IL (US)

( * ) Notice: Subject to any disclaimer, the term of this patent is extended or adjusted under 35 U.S.C. 154(b) by 0 days.

(21) Appl. No.: 11/122,777

(22) Filed: May 4, 2005

(65) Prior Publication Data

US 2005/0284924 A1    Dec. 29, 2005

Related U.S. Application Data

(60) Provisional application No. 60/612,280, filed on Sep. 21, 2004, provisional application No. 60/569,031, filed on May 6, 2004.

(51) Int. Cl.
*G06K 7/10* (2006.01)

(52) U.S. Cl. .................................. 235/472.01

(58) Field of Classification Search ............ 235/472.01
See application file for complete search history.

(56) References Cited

U.S. PATENT DOCUMENTS

| | | | |
|---|---|---|---|
| 5,120,117 A | 6/1992 | Williams | |
| 5,493,654 A * | 2/1996 | Gopher et al. | ................ 341/22 |
| 5,522,323 A | 6/1996 | Richard | |
| 5,630,566 A | 5/1997 | Case | |
| 5,661,539 A | 8/1997 | Sheedy | |
| 5,748,184 A * | 5/1998 | Shieh | ........................ 345/173 |
| 5,886,685 A | 3/1999 | Best | |
| 6,076,928 A | 6/2000 | Fateh et al. | |
| 6,128,004 A | 10/2000 | McDowall et al. | |
| 6,227,615 B1 | 5/2001 | Newhouse et al. | |
| 6,244,711 B1 | 6/2001 | Fateh et al. | |
| 6,327,787 B1 * | 12/2001 | Bonzagni et al. | ............. 33/512 |
| 6,345,893 B2 | 2/2002 | Fateh et al. | |
| 6,592,223 B1 | 7/2003 | Stern et al. | |
| 6,726,112 B1 | 4/2004 | Ho | |
| 6,882,851 B2 | 4/2005 | Sugar et al. | |
| 7,113,393 B2 | 9/2006 | Kirchhoff | |
| 2001/0015792 A1 | 8/2001 | Fateh et al. | |
| 2002/0087121 A1 | 7/2002 | Slishman | |
| 2002/0149198 A1 * | 10/2002 | Legg | ......................... 283/115 |
| 2003/0042380 A1 | 3/2003 | Hagglund et al. | |
| 2003/0052164 A1 | 3/2003 | Higginson | |
| 2003/0197682 A1 | 10/2003 | Huang | |
| 2004/0010328 A1 * | 1/2004 | Carson et al. | ................ 700/90 |
| 2004/0195876 A1 | 10/2004 | Huilban | |
| 2004/0210447 A1 | 10/2004 | Zingarelli | |
| 2004/0227728 A1 | 11/2004 | McAlindon | |
| 2005/0116514 A1 * | 6/2005 | Bufkin | ....................... 297/161 |
| 2005/0225217 A1 | 10/2005 | Nay | |

\* cited by examiner

*Primary Examiner*—Michael G. Lee
*Assistant Examiner*—Tae W. Kim
(74) *Attorney, Agent, or Firm*—Townsend and Townsend and Crew LLP

(57) ABSTRACT

A coding scheme is provided that relates to a dimension of a user. The dimension may be a hand size. Depending on the dimension, a code in the coding scheme may be determined. The code indicates an optimal ergonomic setup for a user. A user may thus use the determined code to adjust the product to a position corresponding to the code. At this position, the product may be in an optimal ergonomic setup for the user. Alternatively, the user may select a product according to the determined code.

20 Claims, 16 Drawing Sheets

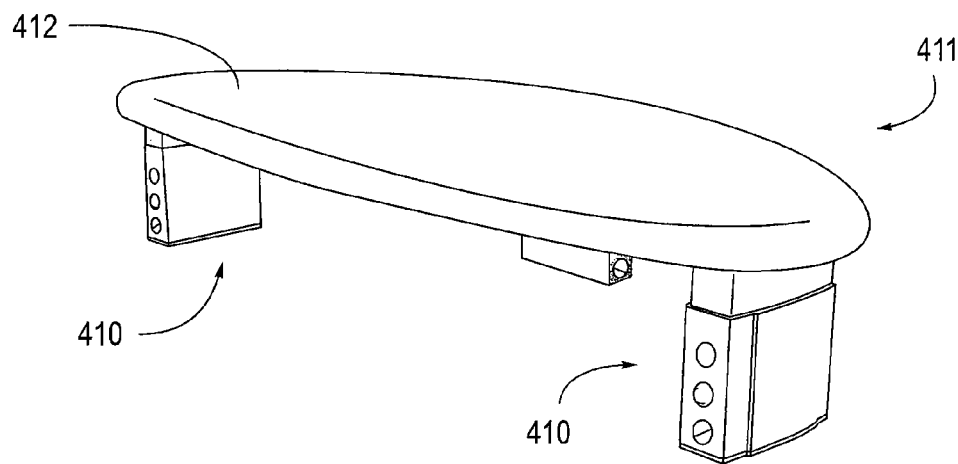
FIG. 8(a)
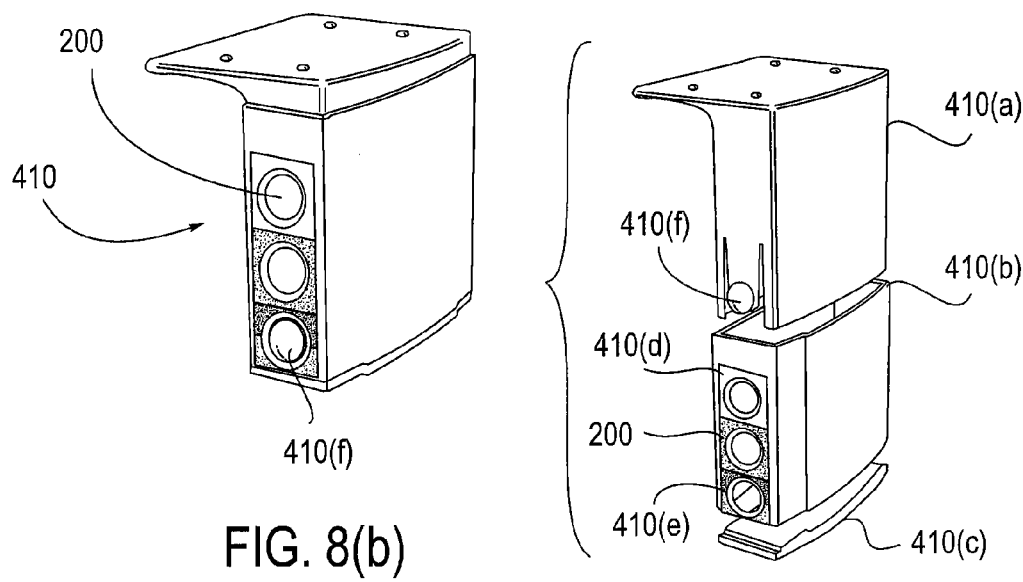
FIG. 8(b)
FIG. 8(c)

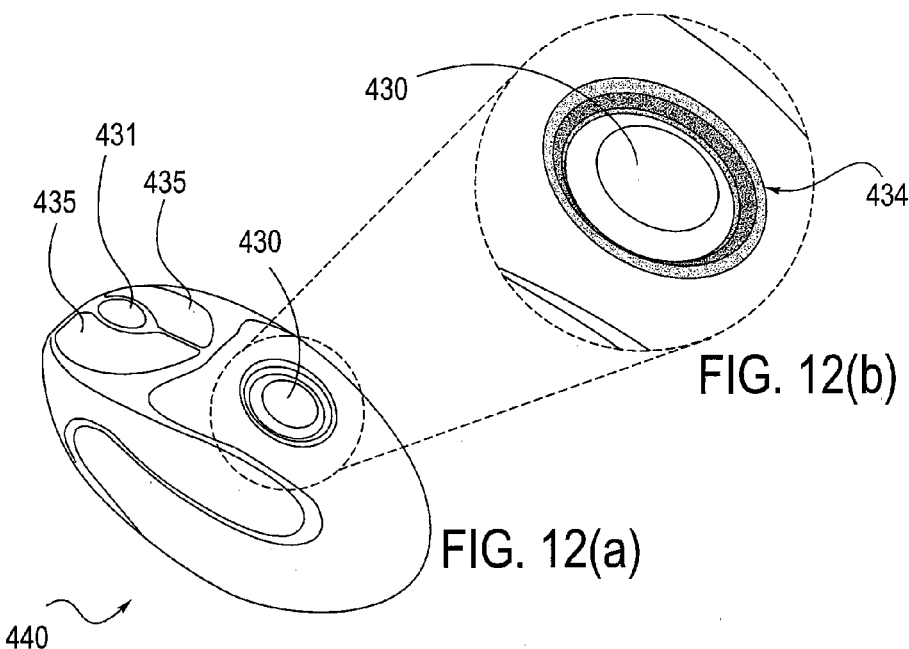
FIG. 12(b)
FIG. 12(a)
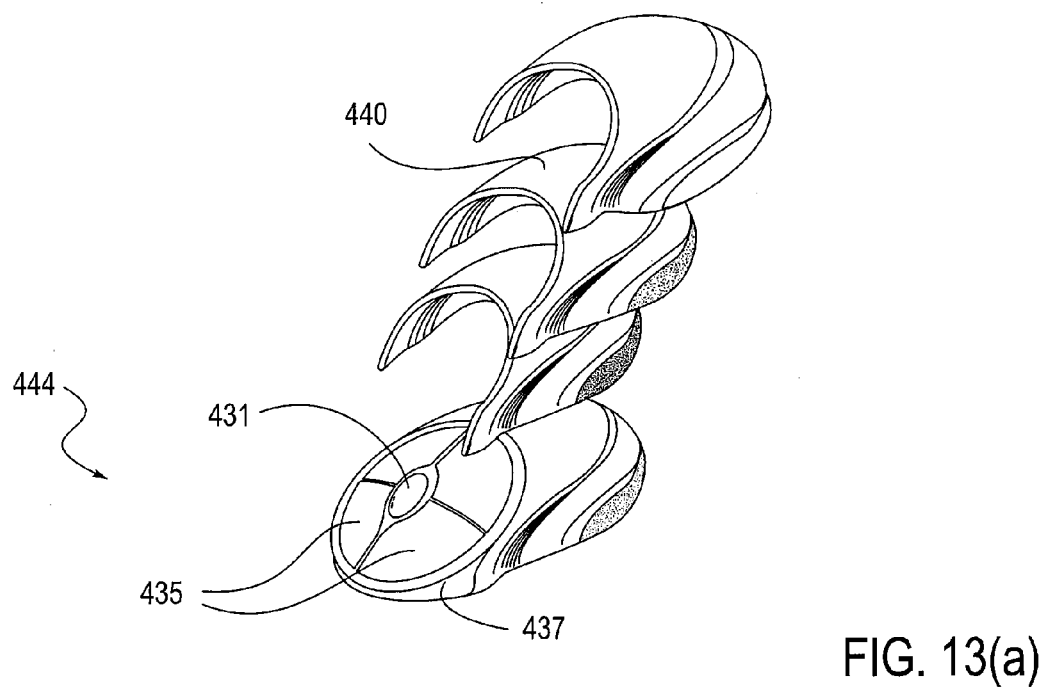
FIG. 13(a)

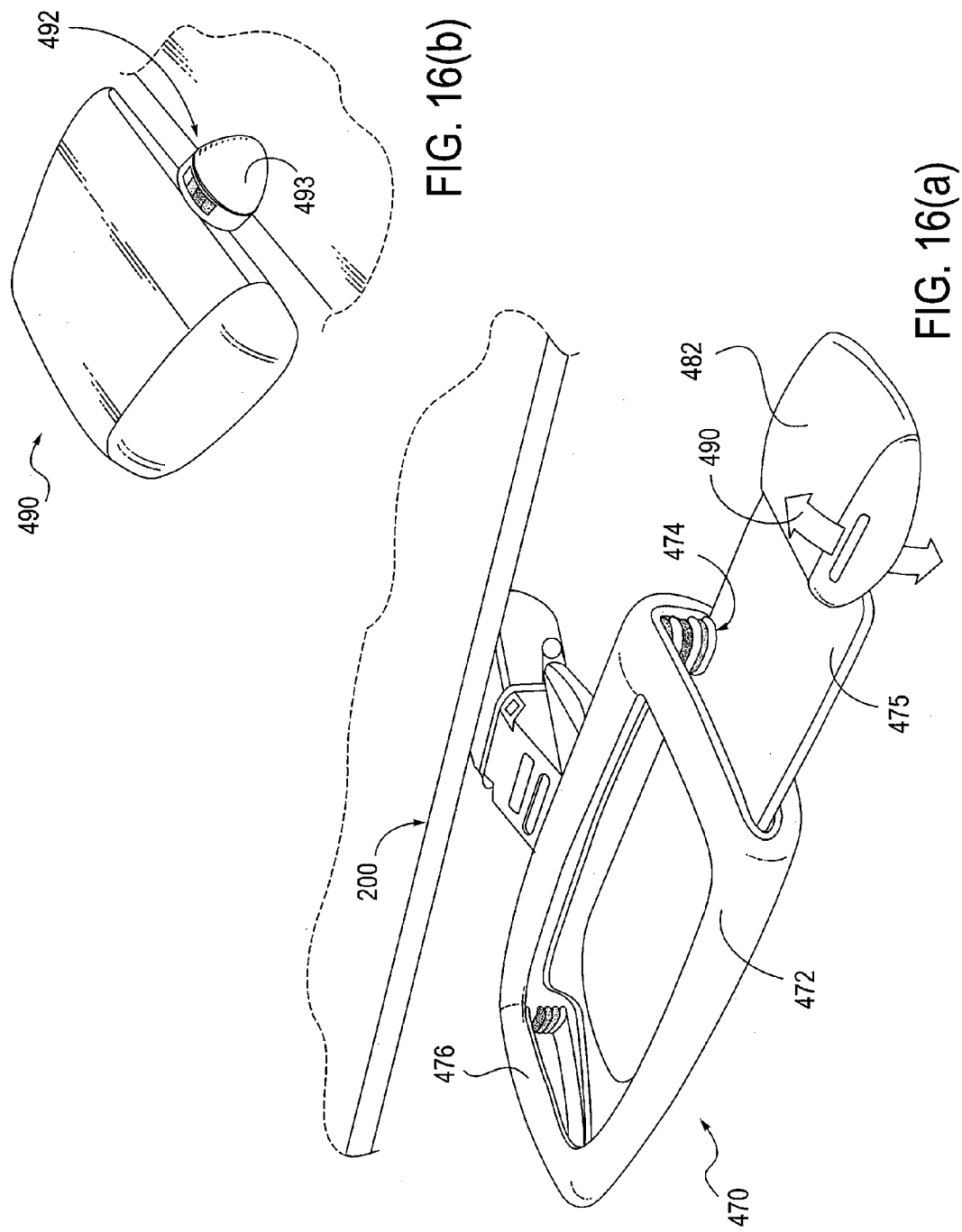

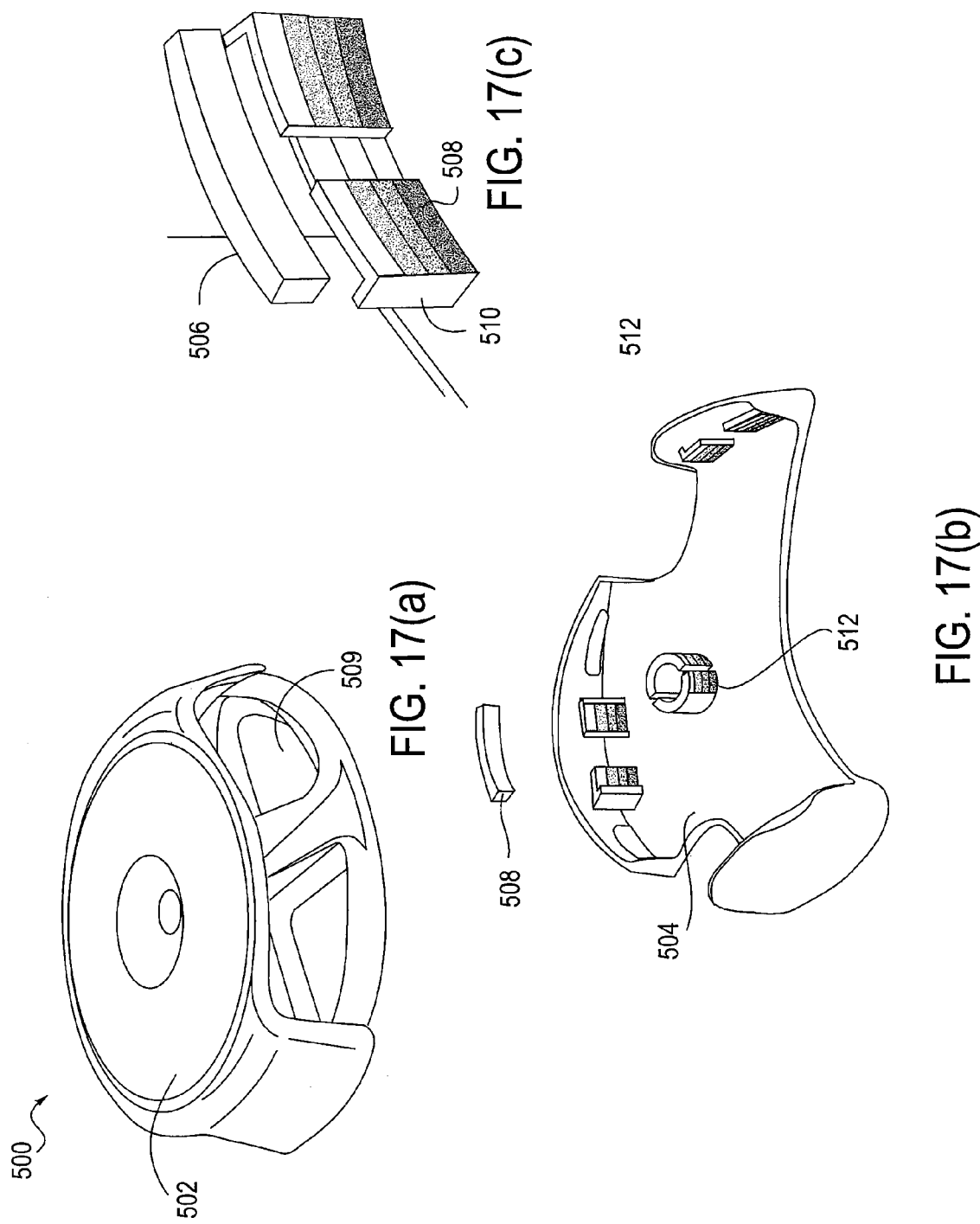

US 7,188,772 B2

METHOD FOR DETERMINING AN OPTIMAL ERGONOMIC SETUP

This patent application is a non-provisional of and claims the benefit of the filing dates of U.S. provisional patent application Nos. 60/612,280 filed on Sep. 21, 2004 and 60/569,031 filed on May 6, 2004, all of which are herein incorporated by reference in their entirety for all purposes.

BACKGROUND OF THE INVENTION

Ergonomics relates to a discipline of dealing with the interaction between a worker and the worker's work environment. An ergonomic hazard is a workplace condition that places a worker at an increased risk of developing a musculoskeletal injury or which would otherwise increase the likelihood of other work performance problems. For example, one ergonomic hazard is an improperly positioned computer keyboard. It is well known that an improperly positioned keyboard and continuous typing using the improperly positioned keyboard may result in carpal tunnel syndrome.

To address the problem of ergonomic hazards, workplace tools such as chairs, trays, monitors, etc. are desirably positioned in an ergonomically optimized manner. Many large corporations hire ergonomic specialists to help workers adjust their work tools to optimal ergonomic positions to minimize injury and maximize comfort.

While ergonomic specialists are effective, many average consumers cannot afford to hire ergonomic specialists. Moreover, even if they could afford ergonomic specialists, ergonomic specialists are not always readily available. Even if they are available, the process of adjusting (and installing) each and every workplace tool for a worker is a time consuming process even for an ergonomic specialist. Also, even if an ergonomic specialist is used, workplace tools can be moved over time due to cleaning personnel, etc. After the tools have been moved, a user will have a difficult time re-adjusting those workplace tools to their optimal ergonomic positions.

While many commercially available products are characterized as "ergonomic," they are in fact often used improperly, because consumers do not have enough guidance on how to properly position or use them. For example, there are many commercially available "ergonomic" chairs, which are capable of being adjusted to different heights. However, the chair manufacturers do not tell the consumers how their chairs should be adjusted so that they are positioned in the most ergonomically effective manner. Consumers often think that their chairs are being used in the most ergonomically effective way. However, they may not be used in the most ergonomically effective way. For example, although a consumer may be using an ergonomic chair, the worker may improperly position the chair too high or too low. The chair may thus be positioned in an ergonomically improper way, even though the worker is using an "ergonomic" chair. Consumers are thus left to guess as to how to position their "ergonomic" workplace tools.

Embodiments of the invention address these and other problems.

BRIEF SUMMARY OF THE INVENTION

Embodiments of the invention are directed to workplace tools and methods that are used to help a user obtain an optimal ergonomic setup.

One embodiment of the invention is directed to an apparatus comprising: a product; and a coding scheme associated with the product, wherein the coding scheme comprises codes corresponding to dimensions of different users and optimal ergonomic setups for the different users. As explained below, the coding scheme may be on the product in some embodiments or may be separated from the product in other embodiments. However, in each case, the product is associated with at least one code in the coding scheme.

Another embodiment of the invention is directed to a system comprising: an apparatus comprising (i) a product, and (ii) a coding scheme associated with the product, wherein the coding scheme includes codes corresponding to different dimensions of different users and optimal ergonomic setups; and a reference guide comprising the coding scheme.

Another embodiment of the invention is directed to a system comprising: an apparatus comprising (i) a product, and (ii) an adjustment guide comprising a plurality of different codes, wherein the codes in the plurality of different codes correspond to different dimensions of different users and optimal ergonomic setups for the users; and a reference guide comprising the plurality of different codes, wherein the reference guide further comprises images of differently sized hands.

Another embodiment of the invention is directed to a method comprising: obtaining an apparatus comprising a product including a plurality of codes associated with the product, wherein the plurality of codes comprises codes corresponding to dimensions of different users and optimal ergonomic setups for the different users; and adjusting the product according to one of the codes in the plurality of codes.

Another embodiment of the invention is directed to a method comprising: obtaining an apparatus comprising (i) a product, and (ii) a plurality of codes associated with the product, wherein the plurality of codes includes codes corresponding to dimensions of different users and optimal ergonomic setups for the users; comparing a dimension of a body part to a guide comprising the plurality of codes to identify a code corresponding to the identified body part; and adjusting the product according to the identified code.

Another embodiment of the invention is directed to a method comprising: obtaining a validation element, wherein the validation element is one in a plurality of validation elements, wherein the plurality of validation elements have dimensions or characteristics corresponding to dimensions of different users and optimal ergonomic setups for the different users; and adjusting or positioning a product using the validation element.

Another embodiment of the invention is directed to a method comprising: obtaining a validation element, wherein the validation element is one in a plurality of validation elements, and wherein the plurality of validation elements have dimensions or characteristics corresponding to dimensions of different users and optimal ergonomic setups for the different users; and adjusting or positioning the product using the validation element.

Yet other embodiments of the invention are directed to specific apparatuses such as keyboard apparatuses.

These and other embodiments of the invention are described in further detail below.

BRIEF DESCRIPTION OF THE DRAWINGS

FIG. 8(a) shows a perspective view of a monitor stand apparatus according to an embodiment of the invention.

FIGS. 8(b)–8(c) respectively show a leg of the monitor stand apparatus shown in FIG. 8(a) in an assembled and an exploded configuration.

FIGS. 12(a)–12(b) show a mouse apparatus according to an embodiment of the invention with an inflatable exterior.

FIG. 13(a) is a perspective view of a mouse apparatus according to an embodiment of the invention. The mouse apparatus can include differently sized housings.

FIG. 16(a) is a perspective view of another keyboard holder apparatus according to another embodiment of the invention.

FIG. 16(b) is a perspective view of a mouse support that can be used in the keyboard apparatus shown in FIG. 16(a).

FIG. 17(a) is a perspective view of a monitor stand apparatus according to an embodiment of the invention.

FIG. 17(b) is a perspective view of a base of the monitor stand apparatus shown in FIG. 17(a).

FIG. 17(c) is a perspective view of a container with an adjustment guide in the base shown in FIG. 17(b).

DETAILED DESCRIPTION

Figure 1A:
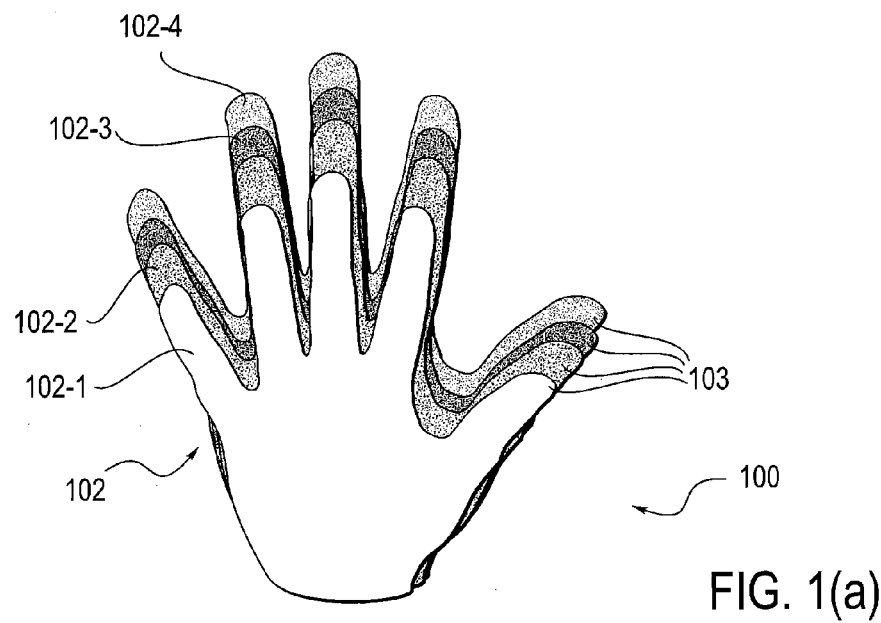
FIG. 1(a) shows a guide including plurality of handprints of different sizes. The handprints may be used to determine a code in a coding scheme according to an embodiment on the invention.

Embodiments of the invention are directed to apparatuses, systems, and methods that are used to obtain optimal ergonomic setups.

One embodiment of the invention is a directed to a method. The method includes obtaining an apparatus comprising a product and a plurality of codes, wherein the codes correspond to the dimensions of different users' body parts and optimal ergonomic setups for the users. The plurality of codes form a coding scheme, which may in turn be part of an adjustment guide that may be associated with the product.

The plurality of codes may also be on a reference guide along with measuring elements for measuring a dimension of a body part. A person can then compare a dimension of a body part such as a hand to a plurality of measuring elements on a reference guide comprising the plurality of codes. The measuring elements may be handprints that are used to measure the size of the hand. After the person determines the optimal measuring element for the body part, the person may then identify a code corresponding to the selected measuring element. Different codes are respectively associated with the different measuring elements. After the person's code is identified, the person can then adjust the adjustable product according to the identified code. Once the adjustable product is adjusted to the person's identified code, the user may optionally use a validation element to verify and/or optimize an optimal ergonomic setup.

Illustratively, a person may obtain a card-shaped reference guide with a yellow handprint, a green handprint, a red handprint, and a blue handprint, wherein each handprint has a different size. The different handprints may be measuring elements, and the different colors associated with the different handprints may be different codes in a coding scheme. The person may determine that his hand size is about the same size as the size of the red handprint in a group of handprints. That person may thereafter identify the color "red" as that person's color for ergonomic adjustment. After the person's color is identified, the person may then adjust his chair apparatus, mouse apparatus, keyboard holder apparatus, and monitor apparatus to a "red" mark in an adjustment guide in each of these adjustable apparatuses. Each adjustment guide comprises a yellow region, a green region, a red region, and a blue region. Each colored region corresponds to a particular adjustable position or adjustable setting in the adjustable apparatus. Once this is done, the person's chair apparatus, mouse apparatus, keyboard holder apparatus, and monitor apparatus are all adjusted so that they are ergonomically optimized for that person.

Any suitable product may be used in embodiments of the invention. Preferably, the product is adjustable. Examples of adjustable products include adjustable chairs, adjustable mice, adjustable keyboard holders, adjustable monitors, adjustable wrist-rests, adjustable portable computers, adjustable keyboards, adjustable handles, adjustable bags, adjustable straps, etc. The adjustable product may be an entire consumer product or a part of a consumer product. For example, an adjustable product according to an embodiment of the invention could be a strap for a bag, or the bag including a strap. In embodiments of the invention, the person using the product or another person (e.g., a manufacturer) may adjust the product.

As noted above, the apparatus may include an adjustment guide that is at or adjacent to the adjustable region of the adjustable product. Together, the plurality of codes in the adjustment guide and the adjustable product may form an adjustable apparatus. Using the adjustment guide on the adjustable product, a person may select the code that is associated with that person and may thereafter adjust the adjustable product to the optimal ergonomic position using the adjustment guide.

The adjustable product may be adjusted in any suitable manner using any suitable adjustment mechanism. For example, in some embodiments, an adjustable product may have at least two connected members that move relative to each other so that a dimension or configuration of the adjustable product is changed. One connected member may be stationary while the other one moves, or both connected members may be movable. An adjustment guide may be provided near a region where the at least two connected members would be adjustable. For example, a chair may have two connected, but adjustable poles, which allow a user to adjust a height of the chair. An adjustment guide with colored regions may be at the region where the two poles are joined and are adjustable to guide a person to the correct ergonomic setting. In yet other embodiments, the adjustable product may have a body and one or more parts that are separable from the body. The parts can be detachably coupled to the body. The one or more parts may be coupled to (e.g., placed on the body, connected to the body, etc.) the body so that the product has the optimal ergonomic setup for a particular person. For example, a mouse may be adapted to use different removable ergonomic gripping structures of different colors and different sizes. Each ergonomic gripping structure may be designed for hands of different sizes. Once a person identifies a particular color associated with that person, one of the ergonomic gripping structures can be coupled to a main body of a mouse to form an ergonomically optimized mouse apparatus. In yet other embodiments, the adjustable product may be moved along an adjustment guide that may be associated with the adjustable product. Examples of different adjustment modes are provided below.

Any suitable reference guide may be used in embodiments of the invention. The reference guide may be two or three-dimensional and typically includes measuring elements and a corresponding coding scheme comprising a plurality of codes. In preferred embodiments, the reference guide is in the form of a card. However, the reference guides according to embodiments of the invention are not limited to cards with hands. For example, instead of a two-dimensional card with images of hands, other reference guides and codes could be used. For instance, another exemplary reference guide could be a ruler with numbers. The numbers may be the codes in this instance, and may be present on various adjustable products. If the user determines that his hand has a height of 5 inches, the user may thereafter locate a "5" mark on an adjustable product and then may adjust the product to an optimal ergonomic position or configuration using the "5" mark. In another embodiment, differently sized three-dimensional grips could be used to measure the dimensions of a hand. The codes may be letters respectively associated with the various grips. These letters can also be present on the adjustable products, and the person can adjust products using a particular letter that is associated with that person.

Any suitable type and/or combination of codes may be used in embodiments of the invention. Examples of codes may include colors, letters, figures, numbers, or other indicia. These may be used by themselves or together with other codes. The codes provide linking information between a person's body part dimension and an adjustment of an adjustable product or a specifically shaped or configured non-adjustable product. The codes may also link different measuring elements associated with body part dimensions to different adjustable positions or configurations for the adjustable products.

The use of a coding scheme with a plurality of codes is particularly advantageous. First, using codes such as color codes, it is easy for a person to link a measured body part dimension to an adjustable position on a product or to select a particular product that is of a suitable size or configuration. Colors, in particular, are easy for a person to visually identify and easy for a person to use as a means for adjustment or selection. Second, once the person determines his or her code, that code may thereafter be used by that person to adjust any adjustable products, or select other products. In embodiments of the invention, once a person determines that the person's code is "blue", that blue color can thereafter be used by that person to adjust all future apparatuses to their optimal ergonomic positions. Third, the codes can be used by a person even if the initial code determined for that person is incorrect. For example, a male may have a "yellow" handsize, but yellow may not be the correct color for that person. Using a validation element (discussed below), the person may determine that the optimal color for that person may be red. That person may then know that the person's proper code is "red" for the adjustment of future adjustable products.

The measuring elements on the reference guide may correspond to the dimensions of predetermined body parts of different users. In some embodiments, the measuring elements may be used to measure a part of a person's body, and may correspond to the outline of a body part. Examples of different body parts that can be measured include hands, feet, arms, legs, etc. The dimensions may correspond to the width, height, circumference, etc. of a particular body part.

Any suitable measuring element may be used in embodiments of the invention. For example, the measuring elements may be intended to circumscribe a body part. For example, the measuring elements may be in the form of outlines of differently sized hands. In other embodiments, the measuring elements may be compared to specific body parts, but need not circumscribe a persons' body part. For example, the measuring elements may be in the form of lines that represent different arm, leg, thigh, etc. lengths. However, the use of the handprints (or other hand dimension(s)) as measuring elements is advantageous, since handprints are easy and intuitive for a person to use.

Humans have different sizes and shapes. However, in a population of users with similar body part dimensions, a substantial majority of those users will use the same ergonomic adjustments. For example, for most individuals, the size of a user's hand approximates other dimensions of the user's body. For example, users having hands with heights (as measured from the longest finger to the crease of the hand) of 7.64 to 7.91 inches can all use the same general ergonomic setups. The measurement of the user's hand will allow the user to not only adjust hand work tools such as computer mice, but also non-hand related work tools such as chairs and computer monitors. Thus, with a single measurement of a single body part, a person can determine optimal adjustments for virtually all of that person's work tools.

In a small number of cases, the ergonomic setup determined using the reference guide may not be optimal. As will be discussed below, in other embodiments of the invention, validation elements may be used by those users to obtain optimal ergonomic setups. Validation elements are discussed in further detail below.

Embodiments of the invention have a number of advantages. First, the concept is simple, intuitive and effective for users. For example, as noted above, a single hand measurement will allow a person to adjust multiple hand-related and non-hand-related work tools to their optimal ergonomic positions. Second, all of the ergonomic adjustments can be performed without the need for an ergonomic specialist. The ergonomic solution described herein is therefore cost effective and convenient for users. Third, the adjustments can be performed more quickly than in the past. For example, an ergonomic specialist need not measure a user and then adjust each and every work tool in a custom manner. In embodiments of the invention, codes can be already present on the adjustable products so all the user needs to do is adjust the products to the code that is specific for that person. No specialized measurements need to take place. The systems, methods, and products according to embodiments of the invention allow a user to "custom fit" his or her office with office products that are all in ergonomically optimized positions. Lastly, adjustments can be made at any time. If work tools move over time due to cleaning personnel, etc., a person can easily re-adjust the work tools without the need for an ergonomic specialist.

FIG. 1(a) shows a reference guide 100 comprising plurality of handprints 102 that may be used to determine a code in a plurality of codes. As shown, various handprints 102 are labeled as handprints 102-1, 102-2, 102-3, 102-4. Although four handprints are shown, it will be understood that any number of handprints 102 may be provided.

Each handprint 102-1, 102-2, 102-3, 102-4 is associated with a different code in a coding scheme and has a size that is different than the other handprints. The outline 103 forming each handprint 102-1, 102-2, 102-3, 102-4 may form a measuring element. The handprints 102-1, 102-2, 102-3, 102-4 are associated with different colors. For example, handprints 102-1, 102-2, 102-3, 102-4 may be associated with or are colored green, blue, red, and yellow, respectively. More or less colors and measuring elements may be used in embodiments of the invention.

Each handprint 102 may also correspond to a certain percentage of males or females and may be sized to capture a range of hand sizes. For instance, green handprint 102-1 may have a height suitable for capturing users with hand sizes between about 6.18 inches and 7.39 inches. This may capture the 5th percentile of the females and the 25th percentile of males. Blue handprint 102-2 may have a height suitable for capturing users with hand heights between about 6.76 inches and 7.64 inches. This may capture the 25th percentile of the females and the 50th percentile of males. Red handprint 102-3 may have a height suitable for capturing users with hand heights between about 7.01 inches and 7.91 inches. This may capture the 50th percentile of the females and the 75th percentile of males. Yellow handprint 102-4 may have a height suitable for capturing users with hand heights between about 7.28 inches and 8.35 inches. This may capture the 75th percentile of the females and the 95th percentile of males. Although a single reference guide may be used for both males and females in this embodiment, in other embodiments, two or more reference guides may be used (e.g., one for males and one for females).

As noted above, for most individuals, the size of a user's hand approximates other dimensions of the user's body. For example, a user's hand size may be used to approximate the user's height, arm length, leg length, etc. The use of a user's hand as an ergonomic measuring tool is particularly preferable because a user can simply place his or her hand on the diagram shown in FIG. 1(a) and can determine his or her code. This allows products, when sold, to include diagrams like the one shown in FIG. 1(a) and a person can easily determine the code that provides that person with the optimal ergonomic adjustment.

Referring to FIG. 1(a), in order to determine a code, a user can place his hand on the handprints 102 shown in FIG. 1(a). The user then determines which handprint 102 most closely fits the user's hand. As shown, handprints 102 are of different sizes. The user may choose a certain handprint 102 if his/her hand substantially fits within one of the handprints.

Once an applicable handprint 102 is determined, the color associated with the handprint 102 is identified by the user. This color is a code in a coding scheme that may be used to adjust certain adjustable products or select a certain product. Sometimes, the color codes may be printed on the products themselves, or may be in the form of stickers on the products.

Other measurement systems may be used to determine a code in a coding scheme. For example, the length of a user's arm from the tip of the middle finger to the elbow may be used to determine the code. Also, the length of a user's leg from the floor to the knee may be used. In yet other embodiments, heights of the users may be used. In these examples, different ranges of measurements may correspond to different codes in a coding scheme. The interrelationship between body part lengths for a majority of individuals was previously determined by the U.S. Army (Natick 1989) in past studies.

Figure 1B:
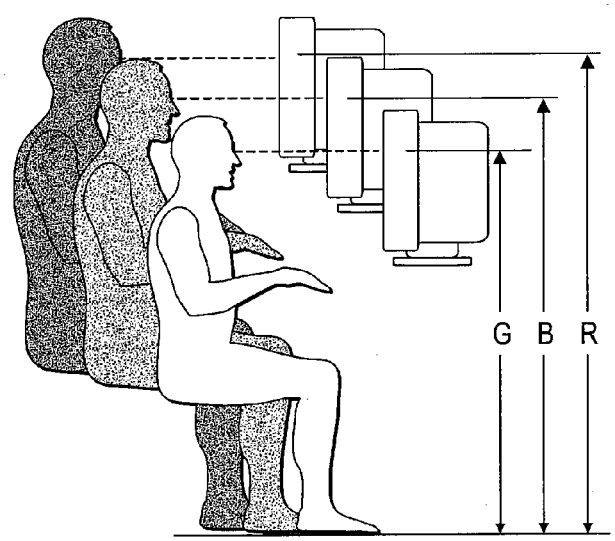
FIGS. 1(b)–1(c) respectively show schematic drawings of various computer monitor heights and chair heights corresponding to optimal ergonomic positions.
Figure 1C:
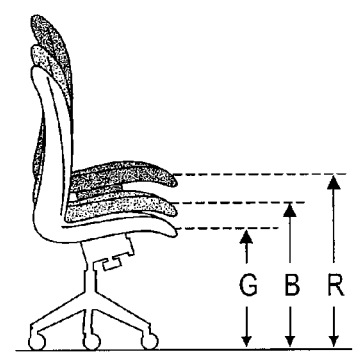

FIGS. 1(b) and 1(c) show how work tools such as monitors and chairs can be ergonomically adjusted using the hand chart in FIG. 1(a).

FIG. 1(b) shows a number of monitor apparatuses with viewing heights associated with green, blue, and red color codes. The height associated with green G can be 41.8 inches from the floor to the person's eye level (which may line up with the topmost portion of a viewing screen of the monitor apparatus). The height associated with blue B can be 47.75 inches from the floor to the person's eye level. The height associated with red R can be 54 inches from the floor to the person's eye level. In these embodiments, it is presumed that a standard desk is used and that most standard desks are of the same height. With this assumption, the monitor apparatuses depicted may have stands that have color codes on them. A person may use the color codes to adjust a monitor to a correct viewing height.

FIG. 1(c) shows a number of chair apparatuses and corresponding heights associated with green, blue, and red color codes. In this example, the height associated with green G may be 15 inches. The height associated with blue B may be 17.25 inches. The height associated with red R may be 19.5 inches. Once a person has determined his or her color code, the person may adjust the height of his or her chair apparatus using the color code. An adjustment guide including green, blue, and red color codes may be at an adjustable region of a base of the chair apparatus.

Using the reference guide shown in FIG. 1(a) and using a person's hand, optimal monitor and chair positions can be obtained. The adjustment of work tools such as chairs and monitors is simple, efficient, and accurate.

Figure 2:
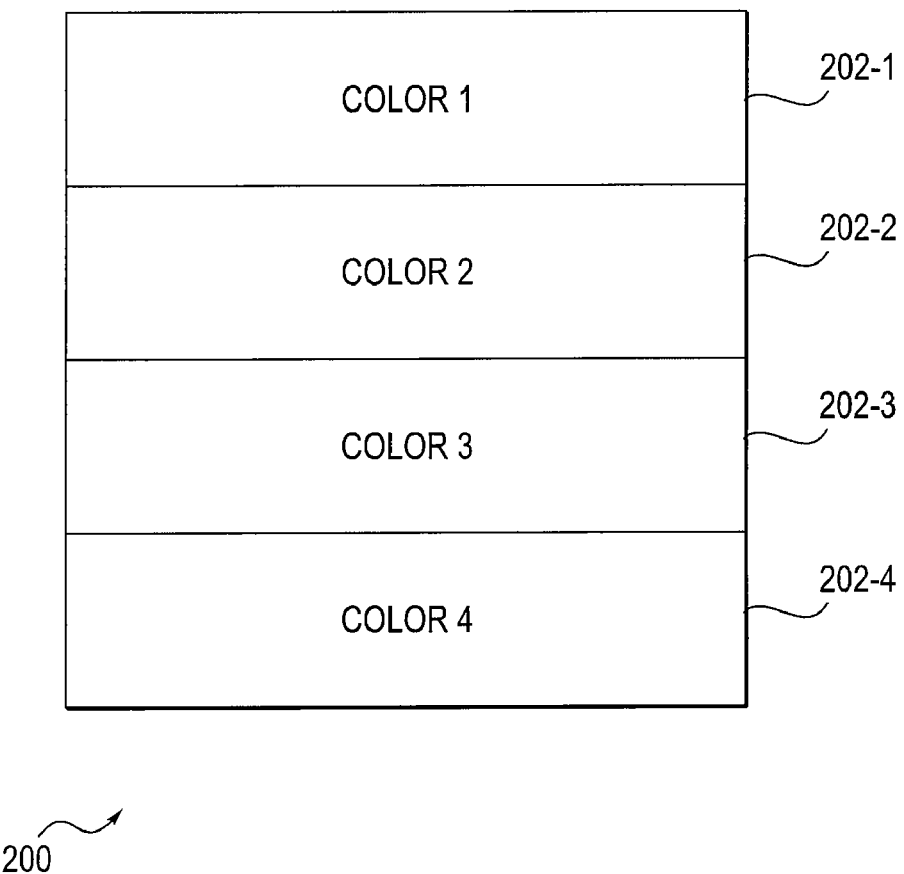
FIG. 2 shows an adjustment guide that shows a coding scheme according to one embodiment of the present invention.

FIG. 2 shows an adjustment guide 200 with a coding scheme according to an embodiment of the invention. The adjustment guide 200 includes a plurality of colors 202-1, 202-2, 202-3, 202-4 which are respectively labeled color 1, color 2, color 3, and color 4. Each color in adjustment guide

200 is a different color. For example, color 1 may be red, color 2 may be orange, color 3 may be blue, and color 4 may be green. More or less colors can be used in other embodiments of the invention. Other coding schemes may also be used. For example, symbols, characters, or other indicia may be used in place of colors.

Although the adjustment guide 200 shown is rectangular, it is understood that other shapes, sizes and configurations of adjustment guides may be used in other embodiments of the invention. For example, the adjustment guide 200 may be shaped as a circle or arc with radial colored bands. In another embodiment, discrete ergonomic gripping structures with respectively different sizes and color codes may be used in a mouse apparatus. The color-coded gripping structures may form an adjustment guide in this embodiment. In yet another example, different slots in a frame of a keyboard holder apparatus may be color-coded. These color coded slots can form an adjustment guide. The form and shape of the adjustment guides according to embodiments of the invention are not limited.

In some embodiments, the adjustment guide 200 may be placed on an adjustable product so that a user may adjust the adjustable product to positions corresponding to colors in the adjustment guide 200. An indicator mark or structure (not shown) may be used to indicate a selected color. For example, the indicator mark could be an arrow pointing to one or more of the codes on the adjustment guide 200. Alternatively, there can be a window (not shown) that shows the code that is selected from the adjustment guide. Codes that are not selected are not shown in the window.

Figure 3A:
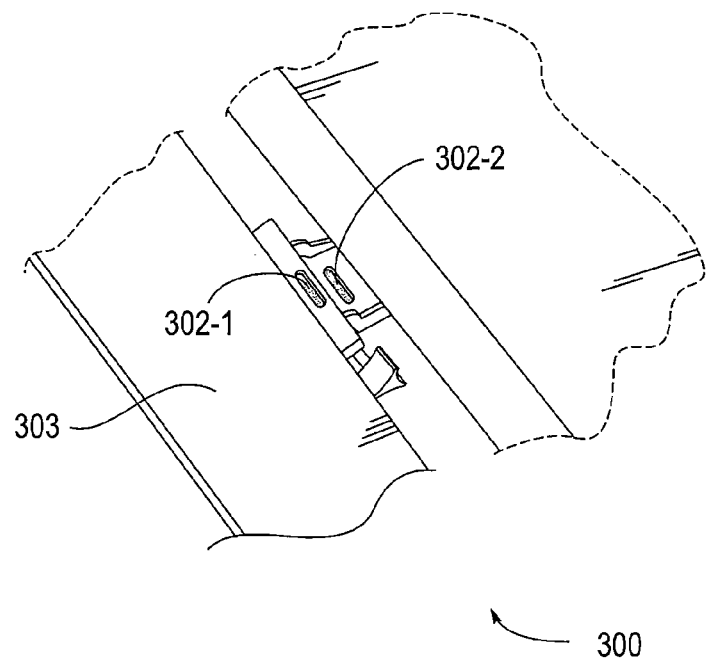
FIG. 3(a) shows a portion of a keyboard holder apparatus according to an embodiment of the invention.
Figure 3B:
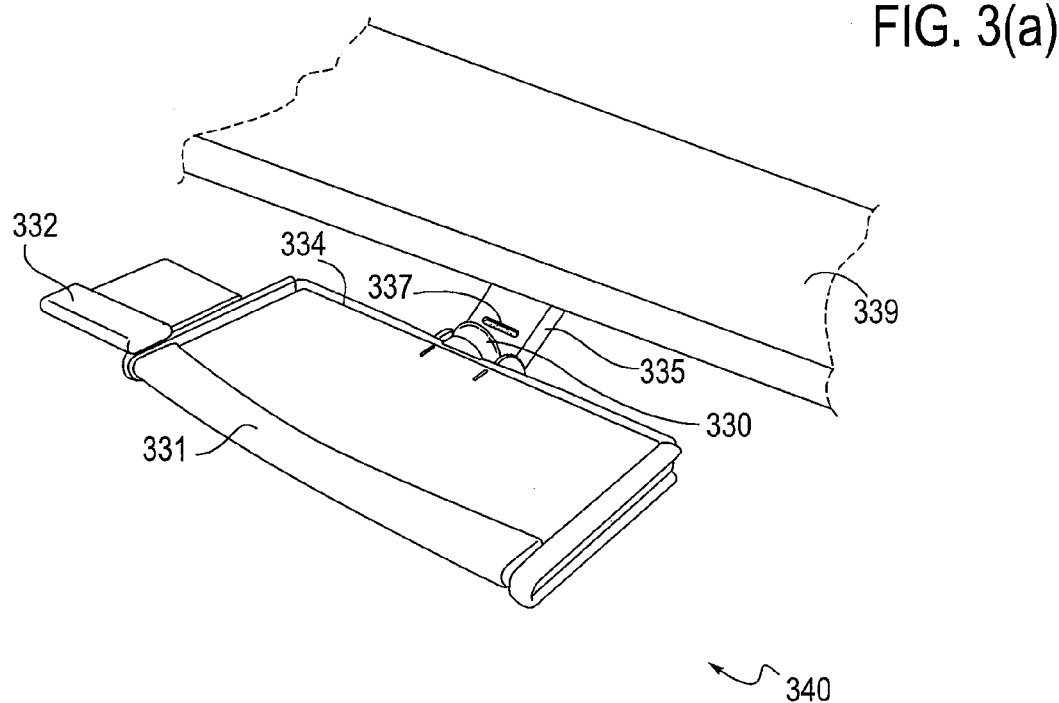
FIG. 3(b) shows another keyboard holder apparatus according to an embodiment of the invention.
Figure 4A:
FIGS. 4(a)–4(f) show images corresponding to a method according to an embodiment of the invention.
Figure 4B:
Figure 4C:
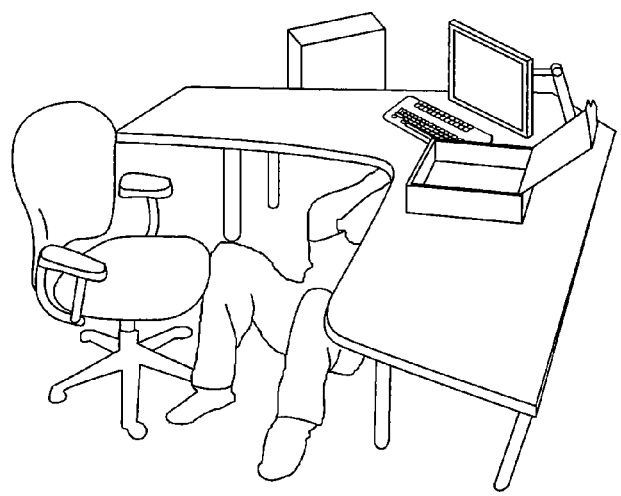
Figure 4D:
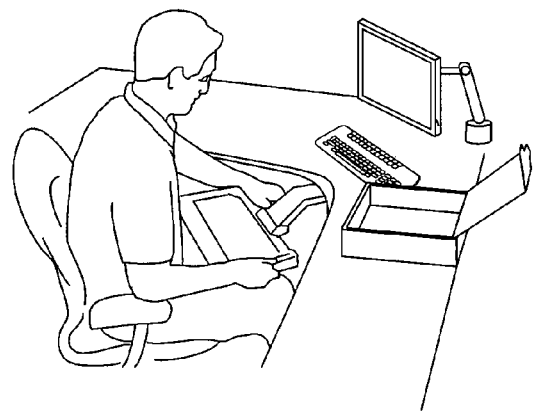
Figure 4E:
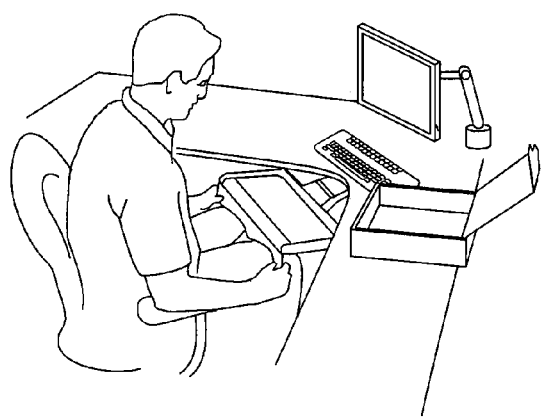
Figure 4F:
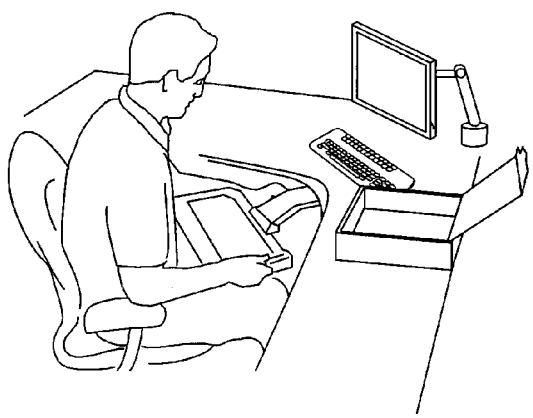

FIG. 3(*a*) shows a keyboard holder apparatus 300 according to one embodiment of the present invention. As used herein, a "keyboard holder apparatus" includes any device that can support or hold a keyboard. The keyboard holder apparatus 300 may be adjustable using the coding scheme. As shown, different codes are shown in one or more windows 302-1, 302-2 on an arm of keyboard holder apparatus 300. In one embodiment, a first window 302-1 may be used for the tilt adjustment of keyboard holder apparatus 300 and a second window 302-2 may be for the height adjustment of keyboard holder apparatus 300.

A user can adjust the keyboard holder apparatus by adjusting the tilt and/or height of the keyboard holder apparatus panel 303 which supports a keyboard (not shown). As the tilt and height of the panel 303 changes, different colors in the coding scheme are shown in windows 302-1, 302-2. When the person's color is shown in windows 302-1, 302-2, the position of the keyboard holder apparatus 300 is ergonomically optimized. A user may then lock the keyboard holder apparatus 300 into that position.

FIG. 3(*b*) shows another keyboard holder apparatus 340 according to an embodiment of the invention. It includes a wedge-shaped platform 334 that includes a tilt adjusting mechanism, which may include a tilt actuator 330. The upper portion of the platform may be a panel. In this example, the tilt actuator 330 can be squeezed by a person to raise or lower a rear portion of the platform 334 so that the platform 334 tilts at an appropriate angle. When the tilt actuator 350 is squeezed, a pneumatic pump raises the rear portion of the platform. A lever (not shown) can be used to lower the rear of the platform. In some embodiments, there may be a pneumatic element between the upper and lower surfaces of the wedge-shaped platform 330. Although a pneumatic raising element is described, it is understood that any other suitable adjustment mechanism may be used to raise or lower a rear upper panel portion of the platform 334.

The keyboard holder apparatus 340 may also include an arm 335. The arm 335 may be like the previously described arm and may allow a person to raise or lower the platform 334. A height actuator (not shown) such as a knob or lever may be provided to raise or lower the platform 334 by moving the arm 335 up or down. Various height adjustment mechanisms are well known and are commercially available. A foam padding border structure 331 and a mouse support 332 are also shown in FIG. 3(*b*).

Advantageously, the keyboard holder apparatuses shown in FIGS. 3(*a*) and 3(*b*) allow a person to adjust both the height and the tilt of a panel supporting a keyboard.

FIGS. 4(*a*)–4(*f*) illustrate a method according to an embodiment of the invention.

FIG. 4(*a*) shows a person opening a box containing a reference guide like that shown in FIG. 1(*a*) and an adjustable keyboard holder apparatus prior to installation on a desk. Like the embodiment in FIG. 1(*a*), the reference guide has a hand chart. FIG. 4(*b*) shows the person measuring his hand against the hand chart. After determining the hand image that is closest to the person's hand image, the person then selects the color associated with the hand image that best matches the shape of the person's hand. FIG. 4(*c*) shows the person installing a tilt keyboard holder apparatus. As noted above, an adjustment guide including a plurality of codes is on an arm of the keyboard holder apparatus. FIG. 4(*d*) shows the person adjusting the tilt of the keyboard holder apparatus to the proper color for the person. FIG. 4(*e*) shows the person using a validation element in the form of a card to validate the distance of the keyboard holder apparatus to the person's thigh. Exemplary validation elements are discussed in further detail below. Then, as shown in FIG. 4(*f*), any additional refinements can then be made by the person. The person can adjust the height of the keyboard holder apparatus to the height suggested by the validation element. As illustrated by FIGS. 4(*a*)–4(*f*), the installation of a keyboard holder apparatus and method for ergonomically adjusting the keyboard holder apparatus is simple and efficient and does not require an ergonomic specialist.

Figure 5:
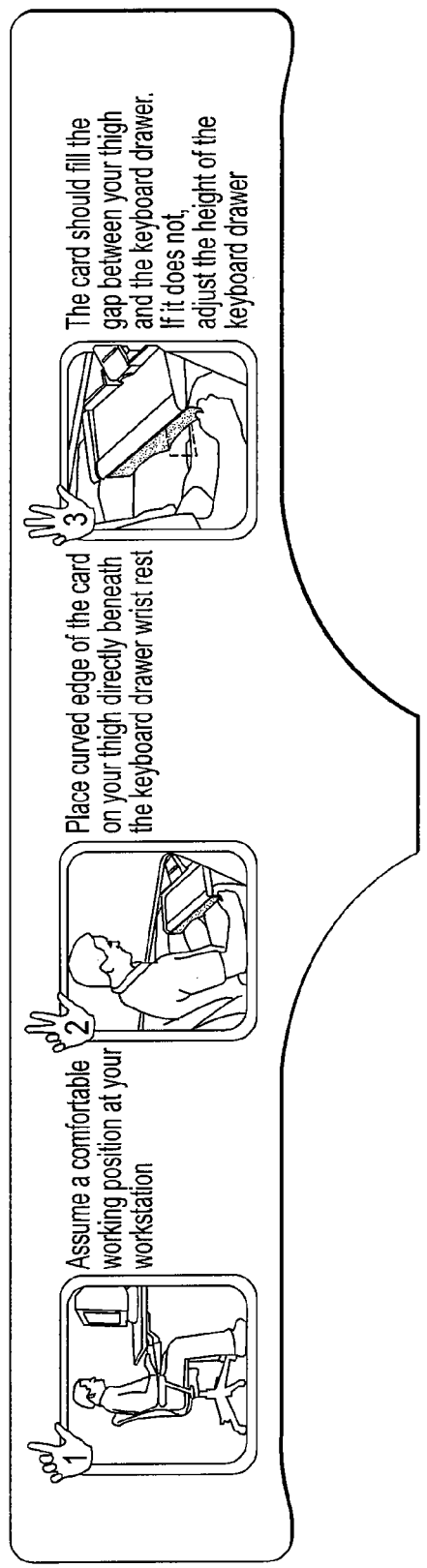
FIG. 5 shows a validation element that can be used in a method according to an embodiment of the invention.

FIG. 5 shows a validation element 380 according to an embodiment of the invention. The validation element 380 can be in the form of a card and has a central portion 382 that can fit between the legs of a person while the person is sitting down in a chair while validating the height of a keyboard holder. As shown in FIG. 5, there are also instructions on how to use the validation element 380. As the instructions indicate, the person first assumes a comfortable working position at a workstation. The person then places the curved edge of the card on the person's thigh directly beneath the keyboard drawer wrist rest. The card fills in the gap between the person's thigh and the keyboard drawer. If the keyboard is not at the proper height, then the height of the keyboard drawer can be adjusted accordingly.

Other validation elements may be used for other adjustable products. For example, a rectangular card may be used to validate the distance between a person's eyes and a monitor. Regardless of the form of the validation element, the validation element may have a dimension corresponding to the optimized ergonomic position for a variety of users.

The validation elements discussed above have been described for use with an adjustment guide on an adjustable product and for verification of a prior adjustment using color codes. However, in other embodiments of the invention, the validation elements may themselves constitute a coding scheme, and the adjustable product need not have an adjustment guide including color codes on it and the validation elements may be used independently of the adjustment guide and may be used as a primary ergonomic adjustment tool. For example, in some embodiments, a person can determine his or her code as described above (e.g., using a reference guide including color codes). After determining that person's code, that person can select the validation element that is associated with that person's code. Differently sized validation elements could included with an adjustable product purchased by a person or may be separately available from the adjustable product. For example, an adjustable product may be associated with four card-shaped validation elements with heights of 2, 3, 4, and 5 inches in some embodiments. One of the validation elements can be selected by a person and used to adjust the adjustable product to an optimal ergonomic position. Accordingly, an embodiment of the invention is directed to a system including an adjustable product and one or more validation elements, wherein the one or more validation elements can have different characteristics (e.g., different sizes, shapes, visual properties, etc.).

Once the validation element is obtained, the user may then adjust the adjustable product (as described above and below) using the validation element without the need to reference an adjustable guide on the adjustable product.

Thus, some embodiments are directed to obtaining a validation element, wherein the validation element is one in a plurality of validation elements, and wherein the plurality of validation elements have dimensions or characteristics corresponding to dimensions of different users and optimal ergonomic setups for the different users, and then adjusting or positioning the product using the validation element. The different validation elements of different sizes may correspond to a coding scheme. Embodiments of the invention may also include systems including a single adjustable product along with a validation element that is one of a group of possible validation elements.

Figure 6:
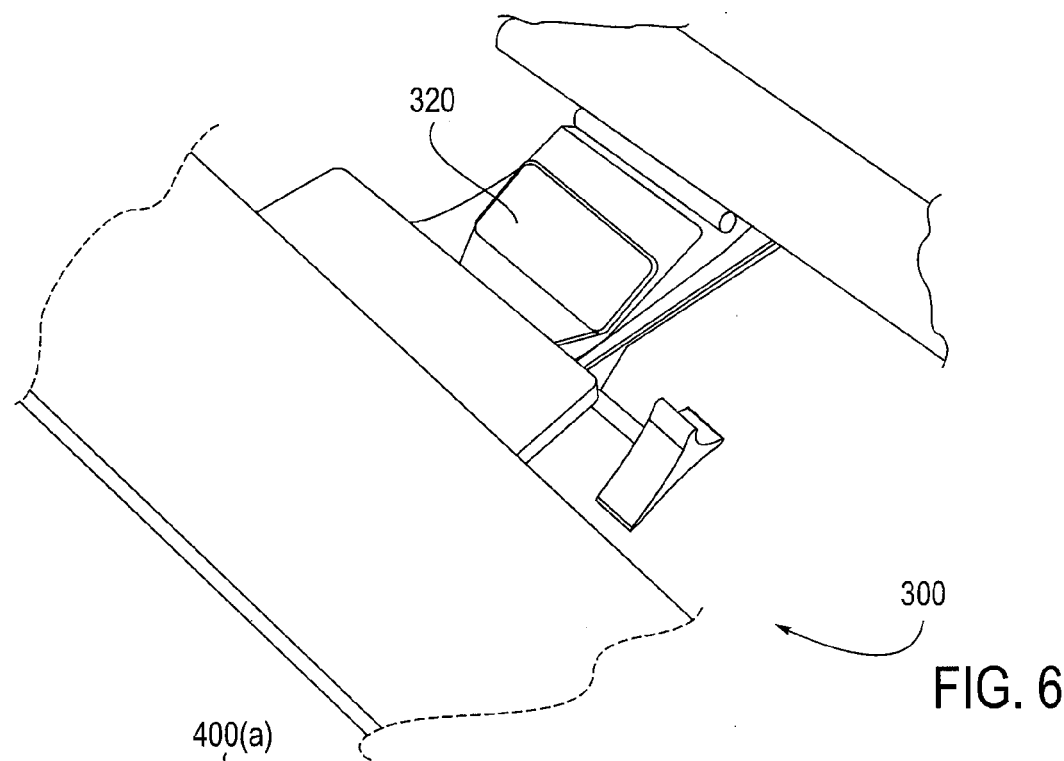
FIG. 6 shows a hologram on an articulating arm of a keyboard holder apparatus.

FIG. 6 shows another embodiment of keyboard holder apparatus 300 according to embodiments of the present invention. As shown, a hologram 320 (or other visual element) is provided on the arm of keyboard holder apparatus 300. A logo in hologram 320 appears when the tilt and/or height for keyboard holder apparatus 300 are properly adjusted.

Illustratively, a user can be positioned in relation to keyboard holder apparatus 300. From this point, a user has a certain viewing angle in relation to hologram 320. Hologram 320 is configured to be visible at a certain viewing angle. Thus, as keyboard holder apparatus 300 is adjusted, the viewing angle is changed and hologram 320 becomes visible to the user at a certain viewing angle. For example, the words "simple fit" may appear when keyboard holder apparatus 300 is properly adjusted, but are not shown when the keyboard holder apparatus 300 is not properly adjusted. This mechanism can be used to find an optimal ergonomic position for the user.

Figure 7A:
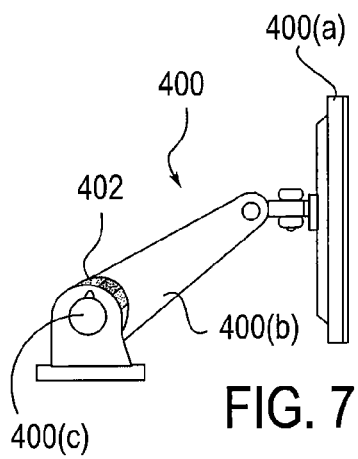
FIGS. 7(a)–7(d) show a monitor apparatus in various ergonomic positions.
Figure 7C:
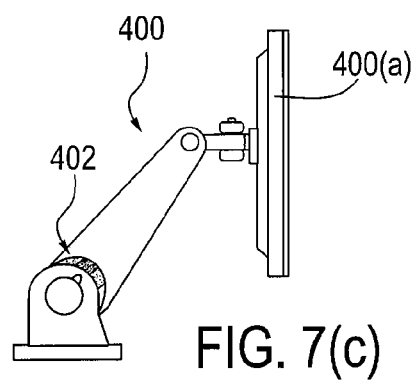
Figure 7B:
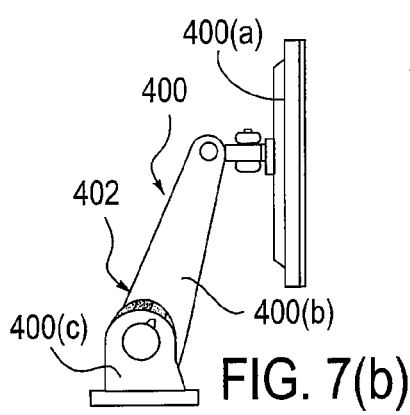
Figure 7D:
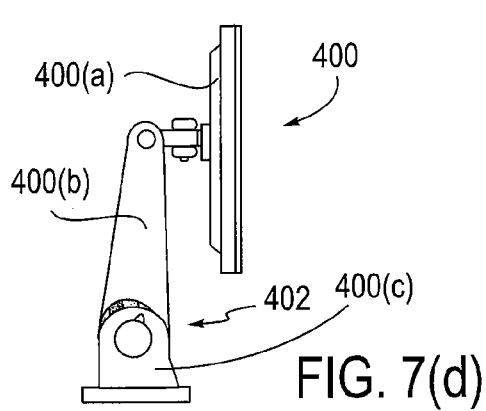

The hologram (or reflective material) 320 may be used in place of or in addition to the previously or later described adjustment guides and reference guides. The hologram 320 can also be used with any other adjustable apparatus including those described herein. For example, the hologram may be used on the monitor apparatus 400 shown, for example, in FIG. 7(a) to provide the proper viewing angle for a person. In this example, a hologram may be placed on a flat panel display portion 400(a) of the monitor apparatus 400 and the display may be tilted until an image appears in the hologram. In this way, the flat panel display portion 400(a) of the monitor apparatus 400 can be positioned in an ergonomically optimal manner. In these embodiments, the hologram can make an adjustable apparatus "self-adjusting" since the user need not use a color coding system. The hologram could alternatively be used as a validation mechanism in conjunction with the previously described coding scheme.

FIGS. 7(a)–7(d) show a monitor apparatus 400 according to an embodiment of the invention in different adjustable positions corresponding to colors in an adjustment guide. The monitor apparatus 400 has a flat panel display portion 400(a), a movable arm 400(b), and a base 400(c) coupled to the movable arm 400(b). As shown, the movable arm 400(b) can move with respect to both the base 400(c) and the flat panel display portion 400(a). The base 400(c) may be secured to or simply placed on a desktop.

An adjustment guide 402 is at the bottom of the movable arm 400(b), and is around the adjustable region joining the movable arm 400(b) and the base 400(c). The adjustment guide 402 may be in the form of a circular band including discrete colored sections such as red, green, blue, and yellow sections. A person may use these colored sections to adjust the movable arm 400(b) to a proper radial position. To assist in this, a marker such as an arrow may be provided on the base 400(c) so that the marker points to the selected colored section.

FIG. 8(a) shows a monitor stand apparatus 411 according to an embodiment of the invention. The monitor stand apparatus 411 has a horizontal portion 412 that bridges two adjustable legs 410. A monitor (not shown) may be placed on the horizontal portion 412.

FIG. 8(b) shows a leg 410 of the monitor stand apparatus in an assembled state. FIG. 8(c) shows the leg 410 in an exploded view. As shown in FIG. 8(c), the leg 410 includes a movable top portion 410(a) and a lower portion 410(b) that houses the top portion 410(a). The leg 410 has a number of apertures and colored regions 410(d) forming an adjustment guide 200 may be around the apertures 410(e). A button 410(f) present at the bottom of the top portion 410(a) can be pushed inward so that the button 410(f) is in the proper aperture 410(e). The button 410(f) secures the top portion 410(a) at desired vertical position so that a monitor on the horizontal portion 412 can be positioned at an ergonomically correct height.

Figure 9A:
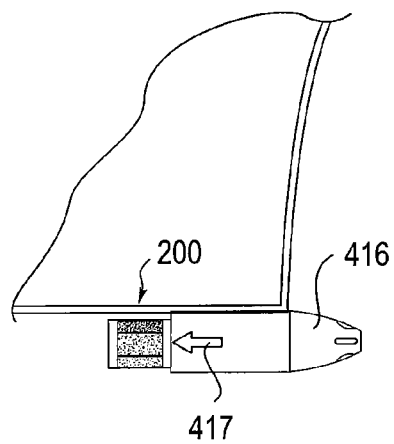
FIG. 9(a) is a perspective view of a document copyholder apparatus according to an embodiment of the invention.
Figure 9B:
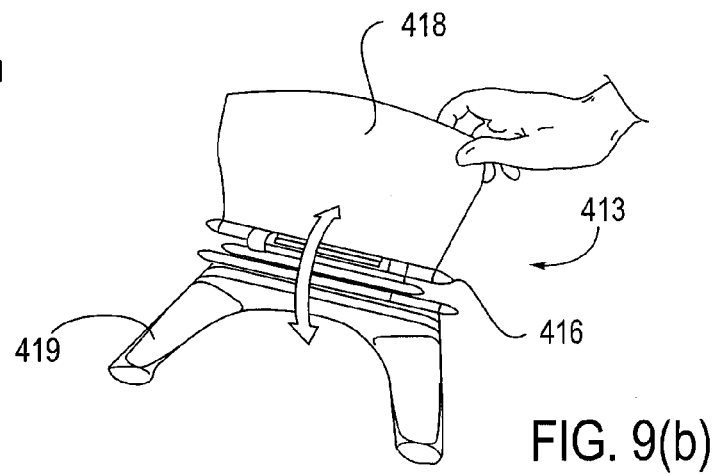
FIG. 9(b) is a close-up frontal view of an adjustment element and an adjustment guide in the document copyholder apparatus shown in FIG. 9(b).

FIG. 9(a) shows a document copyholder apparatus 413 according to an embodiment of the invention. FIG. 9(b) shows a close up view of an adjustment element 416 and an adjustment guide 200 in the document copyholder apparatus. Referring to FIG. 9(a), the document copyholder apparatus 413 has a base 419 and a document holder 418 that is movably coupled to the base 419. An adjustment element 416 in the form of a rotatable knob may be turned to change the angular position of the document holder 418 with respect to the base 419. An adjustment guide 200 comprising a plurality of colored bands may be disposed around a cylindrical part, and the adjustment element 416 can be turned so that an arrow 417 (or other indicia) on the adjustment element 416 points to a colored band in the adjustment guide 200. The selected colored band is associated with a person's optimal ergonomic setting.

Figure 9C:
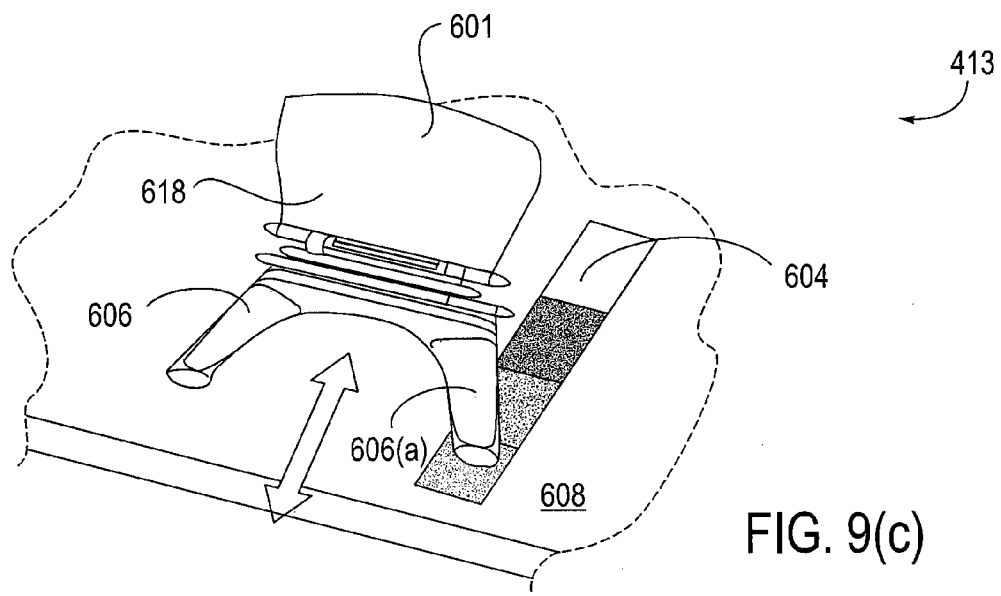
FIG. 9(c) is a perspective view of another document copyholder apparatus according to another embodiment of the invention.

FIG. 9(c) shows another document copyholder apparatus 602 according to another embodiment of the invention. In this embodiment, the document copyholder apparatus 602 includes an adjustable product 601 including a base 606 including a foot 606(a) and a document holder 618 which are relatively movable with respect to each other. The document copyholder apparatus 602 may further include an adjustment element and an adjustment guide as described in the embodiment in FIGS. 9(a) and 9(b).

In the embodiment in FIG. 9(c), however, an additional adjustment guide 604 can be used. Unlike the other embodiments, the adjustment guide 604 is in the form of a flat sheet (with or without an adhesive) with colored bands on it. The adjustment guide 604 is not securely attached to the adjustable product 601 and may lie on a desk surface 608. In this example, the flat sheet is a linear sheet. As shown, the foot 606(a) of the base 606 may be adjusted so that it is placed on the appropriate color that is associated with a person's optimal ergonomic setup.

Figure 10A:
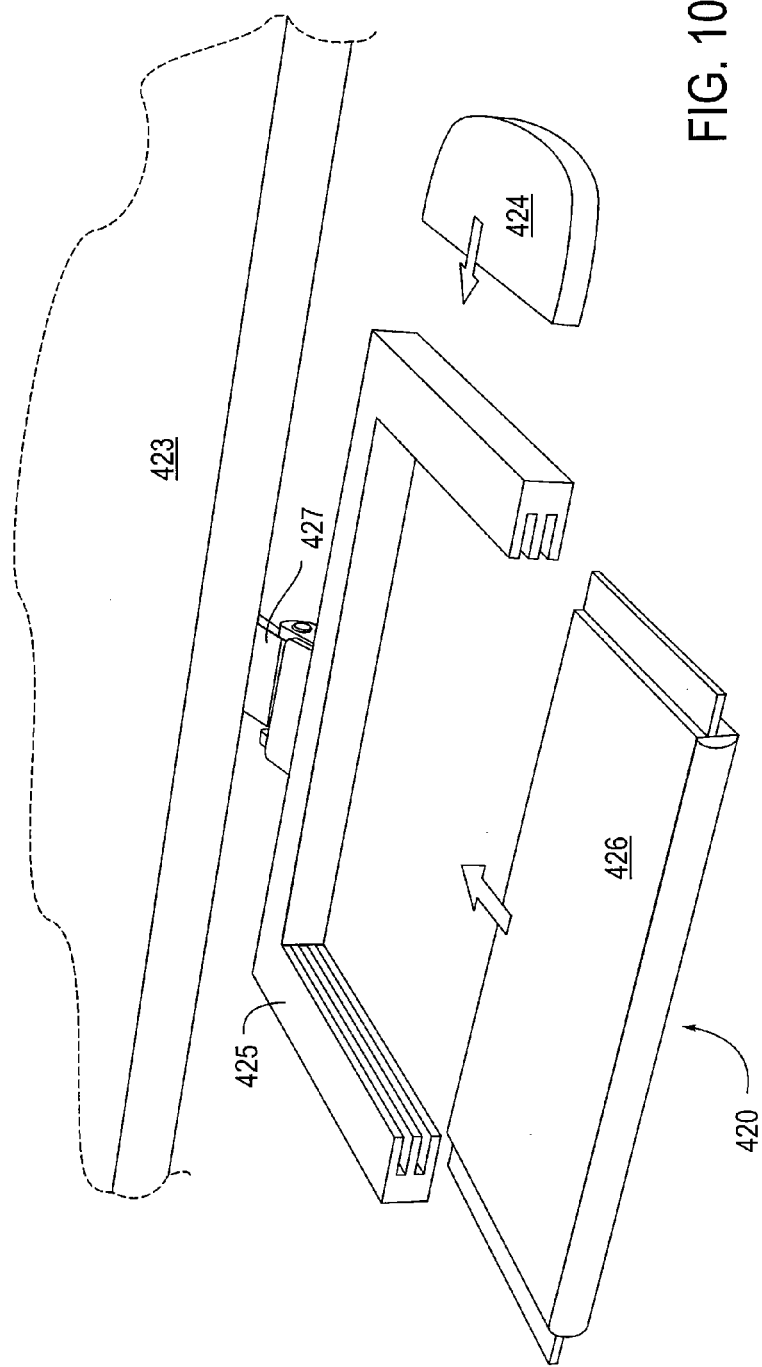
FIGS. 10(a)–10(b) shows an adjustable keyboard holder apparatus according to another embodiment of the invention.
Figure 10B:
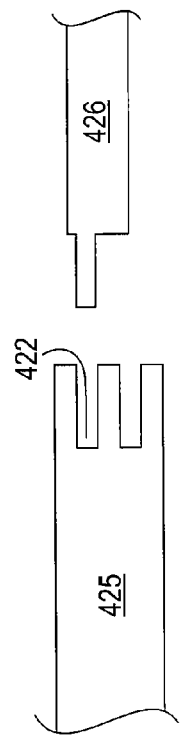

FIG. 10(a) shows another keyboard holder apparatus 420 according to another embodiment of the invention. FIG. 10(b) shows a side, cross-sectional view of an adjustment region of the keyboard holder apparatus 420. As shown in FIG. 10(a), the keyboard holder apparatus 420 has an arm 427 that is coupled to the underside of a desk 423. The arm is coupled to a frame 425 that has an open front portion. A mouse support 424 may be attached to a side of the frame 425. As shown in FIG. 10(b), a panel 426 for supporting a keyboard (not shown) may slide into various slots 422 to allow the keyboard to be at various vertical positions. As in prior embodiments, an adjustment guide (not shown) (e.g., comprising different colored regions) may be positioned near the notches 422 so that a person can put the panel 426 into the slot associated with the person's optimum ergonomic position.

Figure 11A:
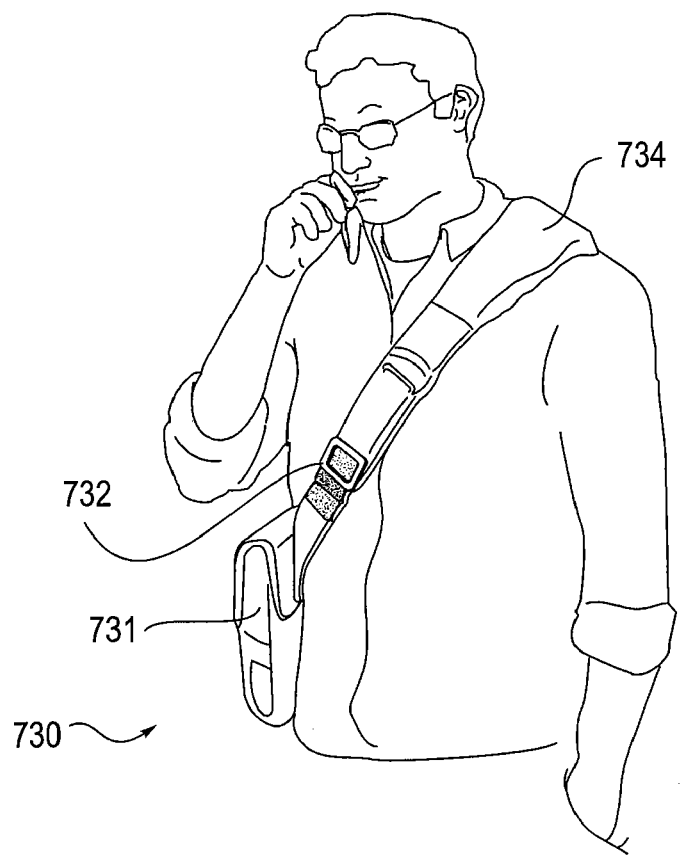
FIG. 11(a) shows a bag apparatus according to embodiment of the invention.
Figure 11B:
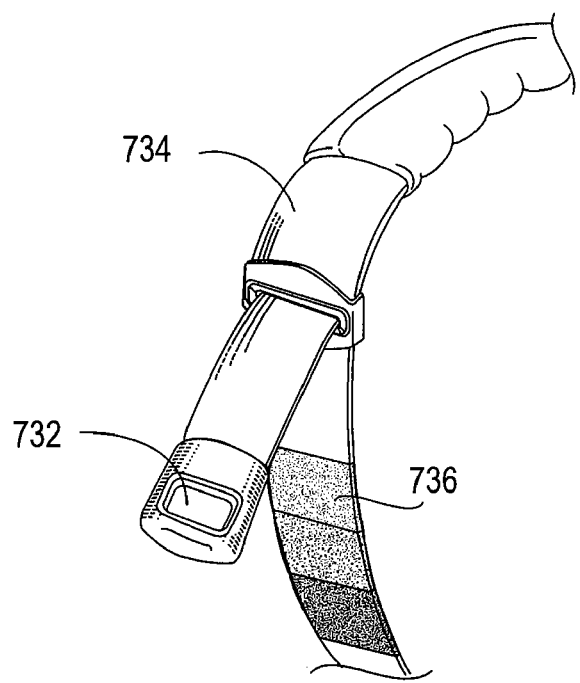
FIG. 11(b) shows a close up view of the strap of the bag apparatus shown in FIG. 11(a).

FIG. 11(a) shows a bag apparatus 730 according to an embodiment of the invention. The bag apparatus includes a bag 731 and an adjustable strap 734 coupled to the bag 731. The strap 734 has an adjustable region comprising an adjustment guide 736 on the adjustable strap 734. As in prior embodiments, a person may adjust the adjustable strap 734 using the adjustment guide 736 so that the ergonomically correct strap position is being used. In this example, the adjustable strap 734 may have a rectangular buckle 732 and the strap portion may be colored with different colors corresponding to different ergonomic positions. The adjustable strap 734 can be adjusted so that the person's code (e.g., the person's color) shows up in the window defined by the buckle 732.

In some embodiments, the bag apparatus may have a side contour that closely fits to the side of a person's body, a cross-brace support, and/or an ergonomic handle. The ergonomic handle may be a two piece handle that fits together to form a one piece handle. A lower portion of the handle has a trough while an upper part of the handle fits in the trough and can pivot in the trough. Such embodiments are described in U.S. patent application Ser. Nos. 10/717,215, 10/870,479, and 10/762,205, which are all herein incorporated by reference in their entirety for all purposes.

FIG. 12(a) is a perspective view of a mouse apparatus 440 according to an embodiment of the invention. FIG. 12(b) is a close-up perspective view of the mouse apparatus 440 of a button 430 present in the mouse apparatus 440. The mouse apparatus 440 includes an expandable (e.g., inflatable) gripping region 432 that surrounds a button 430. A conventional scroll wheel 431 is at the front of the mouse apparatus 400.

Referring to FIG. 12(b), a color-coded adjustment guide 434 has a number of colored rings around the button 430. As the expandable gripping region 432 inflates, different colored rings appear adjacent to the button 430. The gripping region 432 is thus relatively movable with respect to the button 430. After a person determines the person's code using a reference guide (as described above), the person may inflate the gripping region 432 by pressing the button 430 until the colored ring associated with the user's color is adjacent to the edge of the button 430. Then, the size of the gripping region 432 of the mouse apparatus 440 is adjusted so that it is at the optimal ergonomic configuration for the person.

FIG. 13(a) shows another mouse apparatus 444 according to another embodiment of the invention. In comparison to the embodiment shown in FIGS. 12(a)–12(b), in the embodiment in FIG. 13(a), the mouse apparatus 444 includes a number of parts that can be detachably coupled to a main body 437 in the mouse apparatus 444. A scroll wheel 431 and buttons 435 are in the main body 437. The mouse apparatus 444 also includes a main body 450. The gripping structures 440 are different sizes and have different color codes on them. The gripping structure 440 may be in the form of plastic shells that include the outer gripping surface of an assembled mouse apparatus. After a person determines the person's code using a reference guide (as described above), the person may select the appropriate gripping structure 440 and thereafter may attach it to the main body of the mouse apparatus 444.

Figure 13B:
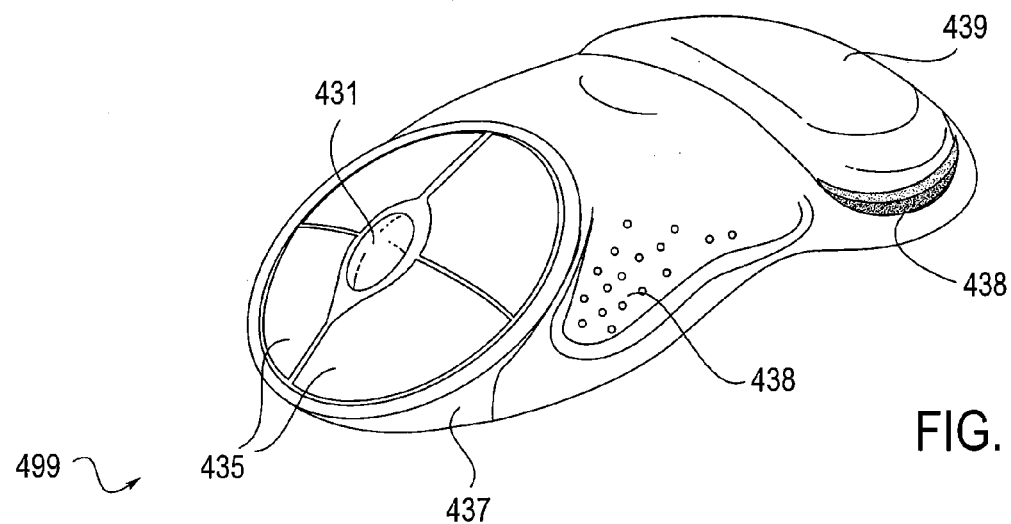
FIG. 13(b) is a perspective view of a mouse apparatus according to an embodiment of the invention. In this example, the mouse apparatus can have differently sized housings and may also have an adjustable wrist-rest region.
Figure 13C:
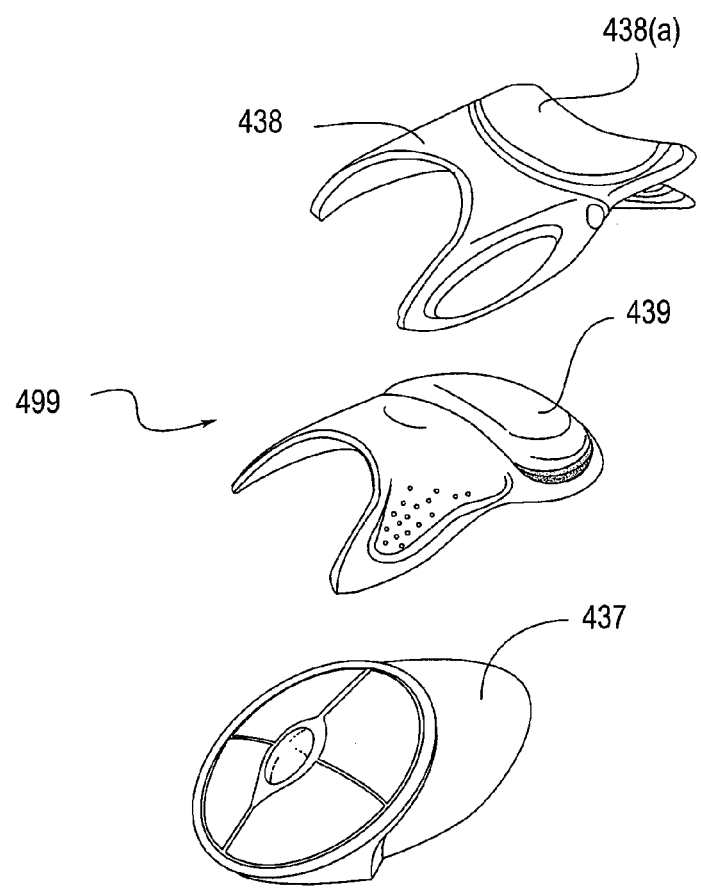
FIG. 13(c) is an exploded view of the mouse apparatus shown in FIG. 13(b).

FIGS. 13(b) and 13(c) show another mouse apparatus 499 according to an embodiment of the invention. The mouse apparatus 499 includes buttons 435 and a scroll-wheel 431 at a front region of the mouse apparatus 499. The scroll-wheel 431 is positioned between the buttons 435. Like the mouse apparatus in FIG. 13(a), a detachable gripping structure 438 may be detachably coupled to a body 437 in the mouse apparatus 499. In the mouse apparatus 499 there can be many detachable gripping structures of different sizes and the person using the mouse apparatus 499 can choose the appropriate gripping structure 438 using a reference guide according to an embodiment of the invention.

In the embodiments shown in FIGS. 13(b) and 13(c), however, the gripping structure 438 has a wrist region 438(a) for holding a wrist-rest structure 439 for supporting the wrist of the person. The wrist-rest structure 439 may be in the form of one or parts that may be detachably coupled to the wrist region 438(a). For example, the wrist-rest structure may be in the form of one or more pieces of foam or one or more gel structures that can be assembled together to provide a proper wrist height for the user. A person may determine the appropriate number of pieces and/or may select the appropriate piece for the wrist region 438(a) using a reference guide according to an embodiment of the invention. In another example, the wrist-rest structure 439 may be coupled to the gripping structure 438 and/or the body 437. For example, the wrist-rest structure 438 may be an inflatable structure like the inflatable structure described above with respect to the mouse apparatus shown in FIGS. 12(a) and 12(b).

FIGS. 13(a)–13(c) show that apparatuses according to embodiments of the invention can use different adjustable housing mechanisms. The adjustable housing mechanisms can provide different ergonomic shapes for different users.

Figure 14:
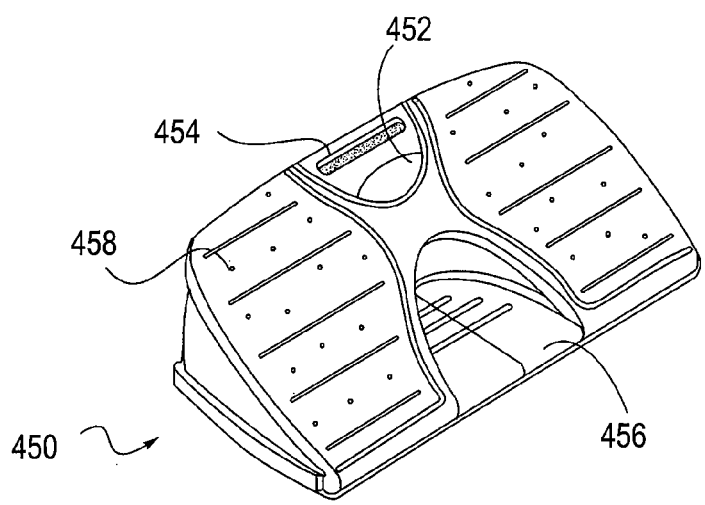
FIG. 14 is a perspective view of a footrest apparatus according to an embodiment of the invention.

FIG. 14 shows a footrest apparatus 450 according to another embodiment of the invention. As shown, the footrest apparatus 450 is wedge-shaped. The footrest apparatus 450 includes foot placement regions 458. A window 454 exposes a color from an adjustment guide in the footrest apparatus. A hologram 452 or other visual device may be used in addition to or in place of the window 454 to verify the correct configuration of the footrest apparatus 450. A foot pedal 456 actuated by a person to "pump" up the footrest to a desired height, angle, or configuration.

As the person steps on the pedal 456, air may be forced into the footrest apparatus 450 to increase the height angle formed by the foot placement regions 458 and the bottom surface of the footrest apparatus 450. As the angle changes, different colors from the adjustment guide may show through the window 454. Once the color associated with the person's optimal ergonomic setting appears in the window 454, the user can stop and the configuration of the footrest apparatus 450 can be set. Alternatively or additionally, a user can step on the pedal 456 until an image shows in the hologram 452. The appearance of the image in the hologram 452 will indicate that the footrest apparatus 450 is configured in its optimal ergonomic position for the person.

Figure 15:
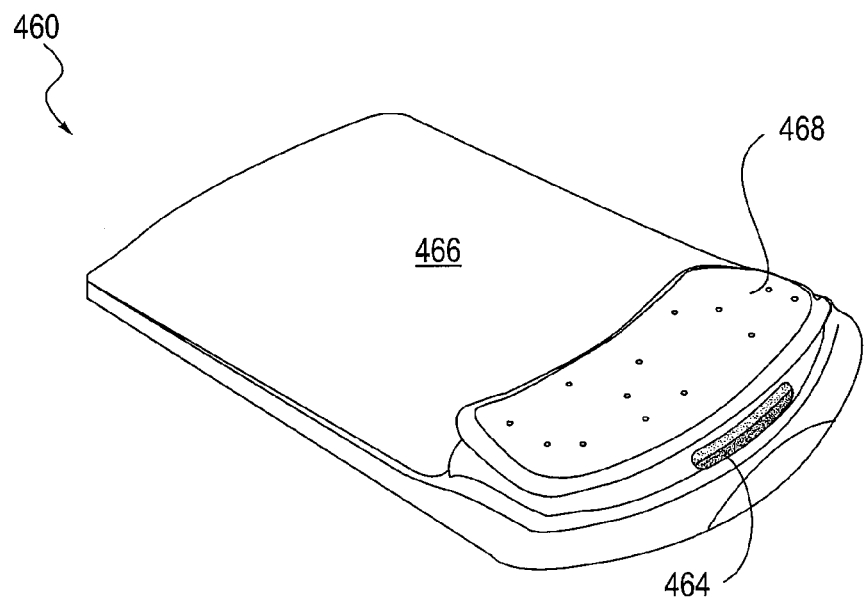
FIG. 15 is a perspective view of a mousepad apparatus according to an embodiment of the invention.

FIG. 15 shows a mousepad apparatus 460 according to another embodiment of the invention. The mousepad apparatus 460 includes a wrist-rest portion 468 at a rear region, and a surface 466 at a front region of the mousepad apparatus 460. The wrist-rest portion 468 allows lateral movement while supporting the person's wrist, and may be inflated like the above described footrest apparatus 450. A window 464 is at the rear of the wrist-rest portion 468 and exposes a colors in an adjustment guide that is in the mousepad apparatus 460. For simplicity of illustration, the actuator(s) that are used to raise and lower the wrist-rest portion 468 is not shown.

FIG. 16(a) shows yet another embodiment of keyboard holder apparatus 470 according to an embodiment of the invention. As shown, slots 474, 476 are provided at the left and right side of the keyboard holder apparatus 470, where each slot corresponds to a code in a coding scheme. For example, there may be three slots where any structure defining the slots may be colored red, green, and blue, respectively. Each slot represents a different height that corresponds to a different ergonomic setup.

The user may insert a panel 475 connected to a mouse tray 490 into a slot that corresponds to a determined code. A keyboard (not shown) may rest on the panel 475. As shown, a front portion of the panel 475 can remain stationary at the front of the keyboard tray 476 while the back of the panel 475 is adjustable up or down to provide a proper tilt angle for the panel 475 and any keyboard that rests on the panel 475. As shown, the panel 475 may be insertable on the right or left side of keyboard holder apparatus 470. The keyboard holder apparatus 470 has a soft full padded frame 472 and may be somewhat wedge-shaped.

As shown in FIG. 16(b), the tilt of mouse support 490 may also be adjusted. An adjustment guide 492 on an arm extending from the panel 475 may be used for this purpose. For example, mouse tray 490 may be rotated such that a color in the adjustment guide 492 lines up with an arrow on the arm 493. The mouse tray 490 may be in an optimal ergonomic setup at this position.

FIGS. 17(a)–17(c) show a monitor stand apparatus 500 according to an embodiment of the present invention. As shown, a base 504 and platform 502 are present in the apparatus 500. A rotatable tray 509 is on the base 504.

As shown in FIG. 17(c), a container 510 is present in the base 504 and has codes 508. A user can also insert blocks 506 on within the container 510 until the height of the blocks 506 reaches the person's code that is printed on the outer surface of the container 510. Once the blocks 506 have reached their proper height, a user may place the platform 502 on the stacked blocks 506 in the base 504. A user can thus raise or lower the platform 502 to an appropriate position based on the person's determined code. Thus, when a monitor (not shown) is placed on the apparatus 500, the monitor is positioned in an optimal ergonomic setup for the user.

In the various embodiments discussed above, adjustable products are described in detail. However, in some embodiments, adjustable products need not be used. For example, in one embodiment, a code in a plurality of codes is determined by a person. As noted above, the codes correspond to dimensions of different users and optimal ergonomic setups for the different users. The codes may be on a reference guide that correlates a person's body part dimension to one of the codes. Any of the above-described codes, reference guides, products, etc., or characteristics thereof can be used in these embodiments and the descriptions of them need not be repeated here.

Once the optimal code is determined by that person, that person can select a product using the determined code. For example, a manufacturer may produce computer mice of four different sizes, and the mice may be respectively colored red, green, blue, and yellow. The person may determine that his code corresponds to "yellow" and that person may thereafter select the mouse with the "yellow" color from among the differently colored and differently sized mice. The person then has a mouse with an optical ergonomic configuration, even though the mouse does not have an adjustable housing. Thus, embodiments of the invention may or may not use an adjustable product.

The process of identifying a code, and then selecting an appropriately sized or configured product may be used for any product. Exemplary products include those described above (e.g., keyboard holders, monitor arms, monitor stands, etc.). The descriptions of such products need not be repeated here.

Thus, a system according to another embodiment of the invention may include (i) a plurality of products, each product including a single code from a plurality of codes in a coding scheme, where the codes indicate an optimal ergonomic setup or configuration for different users, and (ii) a reference guide including the plurality of codes and measuring elements corresponding to the plurality of codes. The measuring elements may be adapted to measure dimensions of different users' body parts. Measuring elements are described above.

Yet other embodiments of the invention are described in U.S. patent application Ser. No. 11/122,777, entitled "Method For Determining An Optimal Ergonomic Setup"; U.S. patent application Ser. No. 11/122,995, entitled "Ergonomic Keyboard Holder Apparatus"; and U.S. patent application Ser. No. 11/112,783, entitled "Over/Underdesk Apparatus. Other embodiments of the invention are directed to docking stations which are described in U.S. Patent Application No. 60/677,870, entitled "Docking Station", filed on May 4, 2005. All of these patent applications are being filed on the same day as the present application and are herein incorporated by reference in their entirety for all purposes.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed.

Moreover, one or more features of one or more embodiments of the invention may be combined with one or more features of other embodiments of the invention without departing from the scope of the invention. For example, any of the embodiments described with respect to FIGS. 1–2 can be combined with the embodiments described with respect to FIGS. 3–17 without departing from the scope of the invention.

A recitation of "a", "an" or "the" is intended to mean "one or more" unless specifically indicated to the contrary. For example, "an adjustment guide" means that one or more adjustment guides may be present.

All patents, patent applications, publications, and descriptions mentioned above are herein incorporated by reference in their entirety for all purposes. None is admitted to be prior art.

What is claimed is:

1. A method comprising:
   obtaining an apparatus comprising a product including a plurality of codes associated with the product, wherein the plurality of codes comprises codes corresponding to dimensions of different users and optimal ergonomic setups for the different users, wherein the plurality of codes is on a two or three-dimensional guide; and
   adjusting the product according to one of the codes in the plurality of codes.

2. The method of claim 1, wherein the plurality of codes comprises a plurality of different colors, each color indicating a different ergonomic position.

3. The method of claim 1, further comprising using the guide comprising the plurality of codes to determine a person's code.

4. A method comprising:
   obtaining an apparatus comprising a product including a plurality of codes associated with the product, wherein the plurality of codes comprises codes corresponding to dimensions of different users and optimal ergonomic setups for the different users; and
   adjusting the product according to one of the codes in the plurality of codes, and wherein the method further comprises using the guide comprising the plurality of codes to determine a person's code, wherein the guide is a card and comprises handprints with different sizes.

5. The method of claim 1, wherein the product is one selected from the group consisting of an adjustable chair, an adjustable mouse, an adjustable keyboard platform, an adjustable monitor stand, an adjustable footrest, an adjustable computer case, an adjustable copyholder, an adjustable monitor arm, and an adjustable mousepad.

6. The method of claim 1, wherein adjusting the product comprises moving a portion of the product.

7. The method of claim 1, wherein the plurality of codes comprises a plurality of different colors comprising red, yellow, green, and blue, and wherein each color indicates a different ergonomic position.

8. The method of claim 1, wherein the plurality of codes is also at an adjustable region of the product.

9. A method comprising:
   obtaining an apparatus comprising a product including a plurality of codes associated with the product, wherein the plurality of codes comprises codes corresponding to dimensions of different users and optimal ergonomic setups for the different users; and
   adjusting the product according to one of the codes in the plurality of codes, wherein the product comprises a body and at least one adjustment element that is physically separable from the body, and wherein adjusting the product comprises placing the at least one adjustment element on the body.

10. The method of claim 1, wherein the product is a keyboard platform.

11. A method comprising:
    determining a code in a plurality of codes, wherein the plurality of codes comprise codes corresponding to dimensions of different users and optimal ergonomic setups for the different users, wherein the plurality of codes is on a two or three-dimensional guide; and
    selecting or adjusting a product using the determined code.

12. The method of claim 11 wherein the plurality of codes comprises color codes.

13. A method comprising:
    determining a code in a plurality of codes, wherein the plurality of codes comprise codes corresponding to dimensions of different users and optimal ergonomic setups for the different users; and
    selecting or adjusting a product using the determined code, wherein the plurality of codes is associated with a plurality of handprints.

14. The method of claim 11 wherein the method comprises selecting the product, wherein the product has the determined code.

15. A method comprising:
    obtaining a validation element, wherein the validation element is one in a plurality of validation elements, and wherein the validation elements in the plurality of validation elements have dimensions or characteristics corresponding to dimensions of different users and optimal ergonomic setups for the different users; and
    adjusting or positioning the product using the validation element, wherein the plurality of validation elements comprise cards of different sizes.

16. The method of claim 15 wherein the product is an adjustable product.

17. The method of claim 15 wherein the validation elements have different colors.

18. The method of claim 15 the validation element is selected using a reference guide.

19. The method of claim 1 wherein the plurality of codes is printed on the guide.

20. The method of claim 1 wherein obtaining and adjusting are manually performed by a user.

* * * * *